United States Patent [19]

Giannini et al.

[11] Patent Number: 4,925,675

[45] Date of Patent: May 15, 1990

[54] ERYTHROMYCIN MICROENCAPSULATED GRANULES

[75] Inventors: Robert P. Giannini, Plantation; Susan M. Fromm, Margate; José Suarez, Miami, all of Fla.

[73] Assignee: hiMedics, Inc., Hollywood, Fla.

[21] Appl. No.: 234,034

[22] Filed: Aug. 19, 1988

[51] Int. Cl.$^5$ ............................................. A61K 9/26
[52] U.S. Cl. ................................... 424/469; 424/470; 424/494; 424/497
[58] Field of Search ............... 424/469, 490, 489, 470, 424/494, 497

[56] References Cited

U.S. PATENT DOCUMENTS

| | | | |
|---|---|---|---|
| 2,738,303 | 3/1956 | Blythe | 424/458 |
| 3,966,899 | 6/1976 | Nakai et al. | 424/468 |
| 4,083,949 | 4/1978 | Benedict | 424/489 X |
| 4,138,475 | 2/1979 | McAinsh et al. | 424/468 X |
| 4,177,254 | 12/1979 | Khan et al. | 424/16 |
| 4,193,985 | 3/1980 | Bechgaard et al. | 424/458 X |
| 4,261,970 | 4/1981 | Ogawa et al. | 424/475 X |
| 4,263,273 | 4/1981 | Appelgren et al. | 424/473 X |
| 4,341,759 | 7/1982 | Bogentoft et al. | 424/21 |
| 4,349,531 | 9/1982 | Mlodozeniec et al. | 424/452 |
| 4,434,153 | 2/1984 | Urquhart et al. | 424/458 X |
| 4,508,702 | 5/1986 | Hsiao | 424/490 X |
| 4,513,019 | 4/1985 | Brancq et al. | 424/489 X |
| 4,587,118 | 5/1986 | Hsiao | 424/468 X |
| 4,606,909 | 8/1986 | Bechgaard et al. | 424/469 |
| 4,642,233 | 2/1987 | Urquhart et al. | 424/468 X |
| 4,649,043 | 3/1987 | Urquhart et al. | 424/468 X |
| 4,659,558 | 4/1987 | Urguhart et al. | 424/458 X |
| 4,666,705 | 5/1987 | DeCrosta et al. | 424/468 X |
| 4,758,437 | 7/1988 | Sonobe et al. | 424/471 |

FOREIGN PATENT DOCUMENTS

| | | |
|---|---|---|
| 0012495 | 6/1980 | European Pat. Off. . |
| 2331375 | 6/1977 | France . |
| 7614310 | 7/1977 | Netherlands . |
| 8300284 | 2/1983 | PCT Int'l Appl. . |

OTHER PUBLICATIONS

Abbott Laboratories, *Erythromycin, Hydrolysis, and Serum Activity*.

Porter, S. C., et al., *The Effect of Choice of Process on Drug Release from Non-Pareils Film Coated with Ethylcellulose*, Proceed. Intern. Symp. Control Rel. Bioact. Mater., 12, 41–42 (1985).

Baker, R., *Analysis of Oral Dosage Form Patents* 1939 to 1985.

*Primary Examiner*—Thurman K. Page
*Attorney, Agent, or Firm*—Venable, Baetjer, Howard & Civiletti

[57] ABSTRACT

The invention disclosed is erythromycin microencapsulated granules activity densities greater than about 0.300 g/ml. These granules are unusually small having diameters less than about 1000 microns. The granules are particularly useful in hand-held flowable material dispensers. A process for manufacturing such granules is also disclosed.

31 Claims, No Drawings

ERYTHROMYCIN MICROENCAPSULATED GRANULES

BACKGROUND OF THE INVENTION

Over the past several years it has become obvious to health professionals and the pharmaceutical industry that optimal therapy with existing drugs has not been achieved with conventional dosage forms (i.e. tablets, capsules, injectables, suppositories) and dosing regimens. The term "optimal therapy" means the safest, most rapid, and most convenient amelioration of any particular disease state. Further, the "safety" of a dosage form or dosing regimen refers to the frequency and severity of side reactions. Improvement in therapy can then be defined as any change in the dosage form or regimen for an existing drug that: (1) reduces the frequency and severity of side reactions, (2) increases the rate at which cure or control is achieved, and (3) decreases the degree of disruption of normal patient activities.

In response to this growing perception, a number of novel drug delivery systems have been developed and brought to market. Some good examples are the transdermal delivery devices such as Nitro-Dur ® (Key Pharmaceuticals), Nitro-Disc ® (Searle), Transderm Nitro ® (Ciba), Clonidine-TSS ® (Boehringer-Ingelheim) and Transderm-Scop ® (Ciba). Other examples are Theo-Dur ® tablets, a sustained release form of theophylline, Theo-Dur Sprinkle ® (U S. Pat. No. 4,587,118) and Slo-Bid ®. Theo-Dur Sprinkle ® and Slo-Bid ® are microencapsulated forms of slow release theophylline that are intended for use in pediatric patients or other patients who may have difficulty in swallowing a tablet. The microcapsules are supplied in hard gelatin capsules. The hard gelatin capsules are opened at the point of use by the care-giver and administered in a soft food.

This form of drug delivery has significant drawbacks. First, there are a small finite number of capsule sizes marketed, and this limits the physician's ability to prescribe an appropriate dose on the basis of a particular patient's weight, severity of disease, and therapeutic response. Second, there is the possibility of tampering which has become a subject of major concern related to the safety of over-the-counter pharmaceutical products.

Flowable material dispensers such as that described in U.S. Pat. No. 4,579,256 were developed to overcome these drawbacks. The Flowable Material Dispenser is an adjustable, metering and dispensing package. The dispenser can accurately deliver a granular pharmaceutical product to a patient by pouring the selected dosage onto a small quantity of soft food contained on a spoon prior to swallowing. The dispenser is child- and tamper-resistant, protects the product from the surrounding environment and precisely delivers an adjustable dose well within the compendial requirements for uniformity of dosage units. However, microcapsules that are suitable for use in the Flowable Material Dispenser must meet certain narrow specifications with regard to average particle size, particle size distribution, shape, and active agent concentration.

These specifications are generally defined as follows:

| | |
|---|---|
| Particle size/size distribution (depending on dispenser design) | A: 710 Microns - 1000 Microns |
| | B: 590 microns - 840 microns |
| | C: 500 microns - 710 microns |
| Activity Density (potency × bulk density) | not less than 0.300 g/ml |
| Appearance | nearly spherical |
| Flow | freely flowing |

Although an acceptable product could be made beyond the limits of these parameters, high potency and small size are required to achieve the necessary bulk density which insures that the largest dose is contained in a volume that is convenient to swallow. Small size is also essential if the particles are to be relatively impalpable when added to soft food. High bulk density allows a dispenser of reasonable size for one hand operation to contain a ten to sixty day supply of drug. Narrow size distribution insures reproducibility of each measured dose and eliminates variation in bulk density due to segregation of sizes. This is critical to a device which measures solid particles by volume. Narrow particle size distribution also implies reproducibility of bulk density from batch to batch. Thus, the same volume will contain the same amount of drug every time in production, which is a new requirement, imposed by the flowable material dispenser but not by prior art delivery systems such as hard gelatin capsules. It is also important that the microcapsules be nearly spherical to impart the flow characteristics that are required at every stage of assembly and use of the dispenser. The nearly spherical aspect of the microcapsules also enhances product elegance.

Presently available conventional pharmaceutically active granules are generally inappropriate for oral administration with semi-solid food or for use in a hand-held flowable material dispenser. These conventional granules are large and create a noticeable gritty mouth-feel for the patient. Large microgranule size also necessitates an increase in the smallest characteristic dimension of the measuring cylinder and the flow channels of the flowable material dispenser if particle bridging is to be avoided. An increase in the smallest characteristic dimension of the measuring cylinder is also necessary if the requirements of the United States Pharmacopeia for Uniformity of Dosage Units are to be met. As those characteristic dimensions increase, so does the overall size of the flowable material dispenser. Each increase in size of the dispenser results in the loss of a degree of convenience in its use. At some microgranule size larger than 18 mesh (1000 microns), the flowable material dispenser becomes too large to be comfortably hand-held and hand-operated.

Conventional granules are also difficult to accurately dispense from a hand-held flowable material dispenser due to the broad size distribution of granules both within and between batches, as well as the lack of uniform shape of the conventional granules. Erythromycin is uniquely suited for incorporation into a flowable material dispenser because of the complexity of its pharmacodynamic and pharmacokinetic profile. It is well known that dose-related gastrointestinal upsets (epigastric distress, nausea, vomiting and diarrhea) occur commonly with erythromycin administration. It is this adverse effect that the present invention is intended to eliminate. It is believed that much of the gastrointestinal distress that occurs during erythromycin therapy is due to overdose and that accurate delivery of the appropriate dose by weight will provide significant therapeutic advantages.

SUMMARY OF THE INVENTION

The present invention relates to pharmaceutically active microencapsulated granules comprising erythromycin and a binder which have an unexpectedly high concentration (average activity density greater than about 0.300 g/ml), small size (less than about 1000 microns diameter), narrow size distribution, and uniformity of shape (spherical). A number of binders or combinations of binders may be used in the erythromycin granules, including hydroxypropyl methylcellulose phthalate, cellulose acetate phthalate, polyvinyl acetate phthalate, polyvinylpyrrolidone, hydroxypropyl methylcellulose, polyethylene glycol, hydroxypropyl cellulose and polyethylene oxide. However, a preferred binder is a mixture of polyethylene oxide and polyethylene glycol.

The invention further relates to a preferred method of manufacturing the erythromycin granules using fluidized bed techniques to apply coatings to seeds. The use of fluidized bed techniques also aids in achieving the granule properties of high concentration, small size, narrow size distribution and uniform shape.

DETAILED DESCRIPTION OF THE INVENTION

The invention relates to pharmaceutically active microencapsulated granules comprising erythromycin and a binder. Such erythromycin granules are particularly useful in flowable material dispensing devices. One such dispensing device is the "Flowable Material Dispenser" disclosed in U.S. Pat. No. 4,579,256 incorporated herein by reference.

In order for pharmaceutically active granules to be used in the above-described dispenser, such granules must exhibit a high concentration of pharmaceutically active agent, a small size, a narrow size distribution and a uniformity of shape, preferably spherical. They must also be resilient enough to withstand packaging on high speed filling equipment and shipment throughout the world. The uniformly spherical granules ensure the accuracy and reproducibility of doses from the dispenser. The properties of high concentration and small size are necessary for convenience of administration by minimizing the amount of granules the patient has to swallow. The high concentration and small size, along with the narrow size distribution of uniformly spherical granules are also desirable so that the granules do not create an unpleasant gritty feeling in the patient's mouth when the granules are ingested with the food on which they are dispensed. Small average size is also necessary if the flowable material dispenser is to be kept small enough to be hand-held and hand-operated.

The erythromycin granules which meet the above concentration, size and shape requirements comprise a starting seed which has an active coating applied thereto. The active coating comprises erythromycin and a binder.

Erythromycin is a well-known antibiotic which is available as white or slightly yellow crystals or powder. It is slightly hygroscopic and has a $pK_a$ of 8.7. Erythromycin is very slightly soluble in water, and freely soluble in alcohol, chloroform, ether and acetone, and moderately soluble in amyl acetate and ethylene dichloride.

Suitable binders for use with the erythromycin include hydroxypropyl methylcellulose phthalate, polyvinylpyrrolidone, hydroxypropyl methylcellulose, polyethylene glycol, hydroxylpropyl cellulose, polyethylene oxide, cellulose acetate phthalate, polyvinyl acetate phthalate and mixtures thereof. A preferred binder comprises a mixture of polyethylene oxide and polyethylene glycol. The use of the polyethylene oxide/polyethylene glycol binder aids in achieving the required granule properties of the high concentration, small size, narrow size distribution, uniform shape, resiliency, and rapid dissolution in basic media.

Polyethylene oxide is a polymer resin having the formula:

where n determines the degree of polymerization and may range from about 2,000 to about 100,000 depending upon the viscosity grade of the resin. Each repeating unit shown above has a molecular weight of 44, and therefore the corresponding molecular weights of the resins range from about 100,000 to about 5 million.

Preferred polyethylene oxide resins for use in microencapsulated granules have molecular weights ranging from about 100,000 to about 900,000, and viscosities of about 10 cps of 5% solution to about 16,000 cps of 5% solution at 25° C. as measured by Brookfield ® viscometer or suitable equivalent instrumentation. Preferred polyethylene oxide resins are supplied as a white powder with a melting point of 65° C. (149° F). Chemically, polyethylene oxide resins are polyethers, are nonionic, and are water soluble. Polyethylene oxide resins are supplied by Union Carbide under the trademark Polyox ®.

The other component of the binder, polyethylene glycol, is also a polymer resin and has the formula:

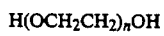

where n is greater than or equal to 4, and generally ranges between 4 and about 210. Polyethylene glycol may be prepared by reacting ethylene glycol with ethylene oxide in the presence of sodium hydroxide (NaOH) at temperatures in the range of 120° C. (248° F.) to 135° C. (275° F.) under a pressure of about 4 atmospheres. Depending on its molecular weight, polyethylene glycol may be a clear viscous liquid or a white waxy solid at room temperature.

Polyethylene glycol with molecular weights between about 190 and about 900 are viscous liquids, while those with molecular weights of about 1000 to about 9000 are waxy solids. The viscosity of polyethylene glycol is measured at 99° C. (210° F.) and ranges from about 4.3 centistokes to about 900 centistokes. The freezing point of polyethylene glycol ranges from about 4° C. (39° F.) to about 63° C. (145° F.). As the molecular weight of polyethylene glycol increases its water solubility, vapor pressure, hygroscopicity, and solubility in organic solvents decreases. In contrast, the freezing or melting range, specific gravity, flash point and viscosity increases as its molecular weight increases. Preferred polyethylene glycols are those with molecular weights from about 1000 to about 9000.

In the preferred binder, polyethylene oxide is present as about 52% by weight to about 72% by weight of the binder and polyethylene glycol is present as about 28% by weight to about 48% by weight of the binder. In a particularly preferred binder, polyethylene oxide of molecular weight 100,000 is present as about 62% by weight of the binder and polyethylene glycol 8000 is present as about 38% by weight of the binder.

In the active coating, the weight ratio of erythromycin to polyethylene oxide/polyethylene glycol binder is preferably between about 5 to 1 and about 15 to 1. It is believed that there is an interaction of weak long range forces such as complexation, hydrogen bonding or Van der Wahl's forces between the erythromycin and the polyethylene oxide/polyethylene glycol binder of the active coating. Such an interaction is theorized based on a very slow dissolution rate for active seeds comprising 92% by weight erythromycin and 8% by weight polyethylene oxide, in simulated intestinal fluid ("SIF"). Both erythromycin alone and polyethylene oxide alone are very soluble in SIF.

Additional evidence of a reaction between erythromycin and the polyethylene oxide/polyethylene glycol binder is found in the fact that the dissolution of an active seed comprising 95% by weight erythromycin and 5% by weight polyethylene oxide increases while the resilience of the seed decreases. Further, when a combination of polyethylene oxide and polyethylene glycol is used as the binder at the 8% level by weight, the dissolution remains rapid but the seeds are not as resilient as with 8% polyethylene oxide alone. This data also implies that the interaction between erythromycin and polyethylene glycol is not as strong as that between erythromycin and polyethylene oxide. Finally, when additional amounts of polyethylene oxide and polyethylene glycol are used as a protective coating, (i.e., intimate contact between molecules of erythromycin and molecules of these substances is avoided) the dissolution is also rapid and resilience increases. The data pertaining to this postulated interaction is presented in Example 14. It can also be seen in Example 10 that the presence of ethyl acetate increased the resilience of seeds manufactured with hydroxypropylmethylcellulose phthalate as the binder. However, that resilience was lost when the ethyl acetate was removed from the process. This indicates that a similar interaction occurs between erythromycin and ethyl acetate.

When applied to the starting seed, the active coating is applied as an active coating composition comprising erythromycin, a binder and a solvent. The coating composition is in the form of a solution or a suspension.

Examples of suitable solvents for use in the coating composition include water, ethanol, methanol, isopropanol, acetone, methylene chloride, chloroform, ethyl acetate, carbon tetrachloride, benzene, methyl ethyl ketone and combinations thereof. Any number of these solvents may be combined to achieve the proper balance between solubility of binder and erythromycin, while still maintaining a pumpable and sprayable viscosity. Such a desired viscosity is between about 5 cps and about 100 cps as measured by Brookfield ® viscometer or suitable equivalent instrumentation. Although the polyethylene oxide/polyethylene glycol binder is preferably dissolved in the solvent, the pharmaceutically active agent may be either dissolved or suspended in the solvent.

The preferred solvent is a mixture of about 70–90% by weight methanol and about 10–30% by weight purified water. A particularly preferred solvent is a mixture of 80% by weight methanol and 20% by weight purified water. The preferred solution or suspension of erythromycin, binder and solvent, contains about 15–40% by weight erythromycin, about 1%–4% by weight polyethylene oxide/polyethylene glycol binder, and the remainder solvent. A particularly preferred solution or suspension contains about 23% by weight to 25% by weight erythromycin and about 2% by weight binder. As high an amount of solids as is possible in the solution or suspension is preferred in order to reduce the process time for manufacture of the granules.

When preparing the active coating composition, the solvent mixture of methanol and water is first mixed. The binder is then added to the solvent mixture and then the erythromycin is blended in to complete the composition.

Commonly used inert starting seeds on which the active coating composition is applied include nonpareil seeds, sucrose crystals, silica gel and ion exchange resins. The preferred size range for inert starting seeds is inversely related to the average daily dose of the drug in question. In the case of high dose drugs like erythromycin, it is desirable to start with the smallest seed possible to obtain the greatest finished drug content. This minimizes the total volume of microcapsules that must be ingested. However, the difficulty encountered in coating discrete seeds smaller than 175 microns increases dramatically. A 60/80 mesh (177 microns-250 microns) starting seed represents the smallest size that can be dealt with without using extraordinary measures. If drug crystals or granulation are to be used as the starting material rather than an inert seed, the preferred starting size would be between 25 and 40 mesh (approx. 420–700 microns). The larger seed size serves to reduce the time required to apply additional drug to the seeds to meet the finished product seed size requirements of diameters less than 1000 microns. Usually, drug crystals or granulation of large size and suitable physical strength are not available on the open market for use as starting materials. Therefore, inert starting seeds are most commonly used in the present invention.

The size of the finished granule is less than about 18 mesh (less than about 1000 microns diameter) and a preferred size is between about 18 mesh and about 25 mesh (about 710 microns to about 1000 microns diameter). The preferred starting seeds for the erythromycin microgranules are (60/80) sucrose crystals. The 25/30 nonpareil seeds are usually used with drugs which require lower daily doses, and the 60/80 sucrose crystals are usually used with drugs which require a higher daily dose.

In one embodiment, the active coating composition is applied to the starting seed by use of a rotor granulator. Examples of conventional rotor granulators are the Vector Freund Spir-A-Flow ® (one embodiment described in U.S. Pat. No. 3,711,319) and the Glatt rotor granulator. In general, a rotor granulator comprises a processing chamber with a rotor at its lower portion. Air is introduced at the level of the rotor for fluidization of the product bed. This air may enter the chamber through the opening between the rotor and the stator and/or through a second opening about midway across the radius of the rotor. This introduction of air results in a spiral and twisting air pattern within the chamber. When the inert starting seeds are introduced into the chamber, the combination of rotor and air circulation pattern is purported to provide higher individual particle densities, and rounder and smoother seeds than conventional fluid-bed systems such as Wurster columns and conventional Glatt fluidized beds.

Once the starting seeds have been fluidized in the rotor granulator, the solution or suspension of binder and erythromycin is introduced through spray guns mounted in the periphery of the stator near the bottom of the product chamber or near the top of the product chamber to spray on the product from above. Although the starting seeds could also be coated using conventional fluidized beds, the rotor granulator is purported to produce a more evenly coated product with a higher concentration of active agent and a greater uniformity of spherical shape of each coated seed.

In addition to the purported benefit derived from use of the rotor granulator, the polyethylene oxide/polyethylene glycol binder also contributes to the unexpectedly high concentration of erythromycin in each coated seed. The high concentration of erythromycin in the coated seeds is not achievable with conventional binders even when such coated seeds are manufactured with a rotor granulator.

Despite the purported benefits of the rotor granulator, it has been found that conventional fluidized bed techniques produce erythromycin microencapsulated granules which meet all of the requirements for use in a hand-held flowable material dispenser. Such fluidized bed techniques are well known to those skilled in the pharmaceutical manufacturing art. With regard to the present invention, fluidized bed techniques are the preferred method of manufacture for erythromycin microencapsulated granules.

After the pharmaceutically active seed has been produced, a protective coating is preferably applied to it. The protective coating is preferably applied to the active seed by using a rotor granulator, although other conventional fluidized beds may be used instead of the rotor granulator. Following application of the protective coating, alternate applications of the active coating and the protective coating may optionally be applied to the coated seed until the desired concentration of erythromycin is present in the microencapsulated granule.

A suitable protective coating comprises a mixture of about 52% by weight to about 72% by weight polyethylene oxide and about 28% by weight to about 48% by weight polyethylene glycol. A preferred protective coating comprises a mixture of about 62% by weight polyethylene oxide and about 38% by weight polyethylene glycol.

The preferred polyethylene oxide is one with a molecular weight of about 100,000 to about 900,000 and the preferred polyethylene glycol has a molecular weight between about 1000 and about 9000. The mixture is produced in the same manner and under the same conditions as the binder described above, and is dissolved in a suitable solvent such as those described above to produce a protective coating composition.

A preferred protective coating composition contains about 10% by weight of the polyethylene oxide/polyethylene glycol mixture and about 90% water as the solvent. Water is the preferred solvent because erythromycin is not highly soluble in water and therefore there is little tendency for the active coating to dissolve or interact with the protective coating composition. The interaction of the erythromycin and the components of the protective coating when brought into intimate contact (as in the active coating composition), was seen to unacceptably slow the dissolution of the finished product in basic media. This protective coating composition also resulted in the strongest granules (i.e. was able to withstand extended processing times).

Another advantage of the protective coating is that it permits the use of acetone as a solvent in an enteric coating composition which is applied to the active seed after a desired concentration of erythromycin has been achieved. Acetone and erythromycin have an undesired reaction which inhibits the removal of acetone from the finished product. The protective coating prevents this reaction. The prevention of this reaction is important because acetone is a preferred solvent for the enteric coating composition, and high levels of residual acetone in the finished product are deemed unacceptable toxicologically and with regard to stability.

The desired concentration of pharmaceutically active agent in each microencapsulated granule is dependent on the nature of a course of therapy (dosage level and duration) for a particular drug, the storage capacity of the device that will be used to dispense the granules and the number of microcapsules that can be conveniently delivered to a spoonful of semisolid food and swallowed. In the case of erythromycin, it is desired that the microencapsulated granules have as high a concentration as possible.

In a preferred embodiment, the erythromycin microencapsulated granules are dispensed from a device such as that described in U.S. Pat. No. 4,579,256. Microencapsulated granules of erythromycin used in these dispensers should have an activity density greater than about 0.300 g/ml and preferably about 0.420 g/ml to about 0.470 g/ml. Activity density is defined as the mass activity of active agent per unit of volume and is equal to the bulk density of the finished product (pharmaceutically active microencapsulated granule) in g/ml multiplied by the potency of the finished product in g/g. In order to achieve the preferred activity density, it is necessary to produce a microencapsulated granule of as high a potency and bulk density as possible.

Since erythromycin has better absorption characteristics in the small intestine than in the stomach, an enteric coating is preferably applied to the erythromycin microencapsulated granules. Such differing absorptive characteristics are thought to be dependent on the comparative acidity of the stomach and the small intestine. The stomach is more acidic (pH of about 1.0) than the small intestine (pH of about 7.0). Erythromycin is not stable in an acidic environment.

An enteric coating may also be applied to granules containing pharmaceutically active agents which are more irritating to the mucosa of the stomach than to the intestinal mucosa. Examples of pharmaceutically active agents with this characteristic are well known to those of ordinary skill in the art and include aspirin and divalproex sodium. Suitable enteric coatings may comprise cellulose acetate phthalate, polyvinyl acetate phthalate, acrylic resins such as Eudragit L ®, shellac, cellulose acetate butyrate, hydroxypropyl methylcellulose phthalate or combinations thereof.

A particularly useful enteric coating for application to the microencapsulated granules comprises between 3% (w/w) and 10% (w/w) hydroxypropyl methylcellulose phthalate. The enteric coating is applied as a enteric coating composition comprising a dispersion of hydroxypropyl methylcellulose phthalate in a solvent comprising either acetone alone or a combination of acetone and methanol. When a solvent combination of acetone and methanol is used, the preferred combinations comprise either about 75% (w/w) acetone and about 25% (w/w) methanol or about 50% (w/w) acetone and about 50% (w/w) methanol. Based on superior dissolution rates and taste-masking properties, a most preferred enteric coating comprises about 6% (w/w) hydroxypropyl methylcellulose phthalate applied in an enteric coating composition comprising a solvent mixture of about 75% (w/w) acetone and about 25% (w/w) methanol. It has been found that this particular ratio of the two solvents produces a finished product of greater stability.

Another suitable enteric coating composition comprises about 5% (w/w) to about 10% (w/w) hydroxypropyl methylcellulose phthalate and a solvent comprising about 75% (w/w) methylene chloride and about 25% (w/w) methanol. The enteric coating applied by this composition is preferably present as about 3% (w/w) to about 10% (w/w) of the microencapsulated granule.

As with the other coating compositions, the enteric coating composition is preferably applied using a fluidized bed technique. Following the enteric coating application, the microencapsulated granules may be subjected to a drying step. The microencapsulated granules are dried in the rotor granulator or fluidized bed processor at a temperature between about 55° C. (131° F.) and about 80° C. (176° F.).

Although the drying step reduces the residual solvent levels to a safe and acceptable level, lower residual solvent levels can be reached by performing an optional second drying step. The optional drying step is performed under a vacuum of 30 mm Hg at about 70° C. (158° F.) for about 23 hours and results in undetectable residual solvent levels in the microencapsulated granules.

An additional optional step after the microencapsulated granules have been dried is the addition of an antistatic agent. About 0.75% by weight (based on the final product weight) of a suitable antistatic agent is added in the fluidized bed or rotor granulator after the final drying step. The fluidized bed is run for about five minutes to distribute the antistatic agent onto the microencapsulated granules. This amount of antistatic agent is sufficient to coat the granules and prevent the granules from sticking to the sides of the flowable material dispenser. The prevention of adherence between the granules and the dispenser serves to reduce variability in dosing which is more common when an antistatic agent is not used.

Suitable antistatic agents include silicon dioxide, polacrilin, talc, magnesium stearate, calcium stearate, stearic acid and combinations thereof. The preferred antistatic agent is silicon dioxide. Silicon dioxide, unlike many of the other suitable antistatic agents, serves the dual purpose of being a moisture scavenger. The elimination of the excess moisture which usually develops from condensation due to climatic changes during shipping and storing, also aids in eliminating variable dosing problems and flow problems with the granules.

The finished erythromycin microgranules may be used in a variety of dosage delivery system, including tablets, capsules and flowable material dispensers. When used in a tablet delivery system, the erythromycin microgranules are compressed or formed into a tablet using conventional pharmaceutical tabletting techniques. When used in a capsule delivery system, the erythromycin microgranules are used to fill water soluble capsules using conventional pharmaceutical capsule manufacturing techniques. When used in a flowable material dispenser delivery system, the erythromycin microgranules are used to fill the flowable material dispenser.

The features and advantages of the invention are further demonstrated by the following examples. In this specification and in the following examples, all parts and percentages are by weight and all temperatures are in degrees centigrade unless expressly stated to be otherwise.

EXAMPLE 1

Preparation of Microencapsulated Erythromycin Granules

A solution of 50.0 grams polyethylene oxide NF and 30.0 grams polyethylene glycol 8000 NF in a mixture of 2400 grams Methyl Alcohol NF and 600 grams Purified Water USP was prepared. The polyethylene oxide/polyethylene glycol 8000 solution was then mixed with 925 grams of Erythromycin Dihydrate USP for seven minutes until a translucent solution ("active coating composition") was formed. Another solution was made from 19.1 grams Polyethylene Oxide NF and 11.5 grams Polyethylene Glycol 8000 NF in 275.4 grams Purified Water USP ("protective coating composition").

The active coating composition was applied (sprayed) onto 500 grams of Sucrose NF (starting seeds) to form active seeds. The starting seeds were 60/80 mesh size. The application of the coating took place after the sucrose had been fluidized in a Vector Freund Spir-A-Flow ® rotor granulator. Once all the active coating composition had been sprayed onto the sucrose, the pump tubing was disconnected and rinsed with Methyl Alcohol NF.

After the pump tubing was reconnected, the protective coating composition of polyethylene oxide and polyethylene glycol 8000 in water was applied (sprayed) onto the active seeds which had been fluidized in the rotor granulator. Once all of the protective coating composition had been applied to the seeds, the product was dried in the rotor granulator at 55° C. (131° F.) for 15 minutes. The product was discharged into a suitable container and labelled Erythromycin Active I Seeds.

A portion (500 grams) of the Active I Seeds were returned to the Spir-A-Flow ®. A second active coating composition was prepared as described above and applied (sprayed) onto the Active I Seeds. After the tubing was rinsed with methanol as described above, a protective coating composition prepared as described above was then applied (sprayed) onto the seeds. The product was dried as described above, discharged into a suitable container and labelled Active II Seeds.

A portion (614 grams) of the Active II seeds were returned to the Spir-a-flow ®. A third active coating composition was prepared using 49.3 grams of Polyethylene Oxide NF, and 29.6 grams of Polyethylene Glycol 8000 NF in a mixture of 236.7 grams of Methyl Alcohol NF and 592 grams of Purified Water USP. The polyethylene oxide/polyethylene glycol 8000 solution was then mixed with 907.5 grams of Erythromycin Dihydrate, USP, for 7 minutes until an active coating composition was formed. The active coating composition was applied to the Active II seeds, after which the tubing was rinsed (sprayed) with methanol. A third protective coating composition which had been prepared with 19.1 grams of Polyethylene Oxide NF and 11.5 grams of Polyethylene Glycol 8000 NF and 275.4 grams of Purified Water USP was applied to the seeds. The seeds were dried at about 55° C. (131° F.) for 15 minutes. The seeds were discharged from the column and labelled Active III seeds. The tubing for the rotor granulator was again rinsed with methanol.

An enteric coating composition was then prepared by mixing 76.6 grams Hydroxypropyl Methylcellulose Phthalate 20073 NF into a mixture of 1091 grams Acetone NF and 364 grams Methyl Alcohol NF. A portion (1200 grams) of the Active III Seed were then fluidized in the rotor granulator, and the enteric coating composition applied by spraying the seeds. When all of the enteric coating composition had been applied, the seeds were dried in the rotor granulator at about 70° C. (158° F.) until a constant product temperature was obtained (58° C., 136° F.) after about 45 minutes.

Finally, 9.6 grams of silicon dioxide NF was added to the dried fluidized granules in the rotor granulator. The rotor granulator was run for about five minutes, after which time the granules were uniformly coated with the silicon dioxide.

The resulting erythromycin dihydrate microencapsulated granules had an activity density of 0.456 g/ml and were of uniform small size and uniform spherical shape. About 90% of the final granules were between 700 microns and 1000 microns in diameter.

Table 1 below, shows the amounts of each ingredient in the final product.

TABLE 1

| Qty. per 250 mg dose of Erythromycin base (mg) | Ingredient | Qty. per Kg Batch size (g) |
| --- | --- | --- |
| 271* | Erythromycin Dihydrate USP | 799 |
| 20.3 | Hydroxypropyl Methylcellulose Phthalate 200731 NF | 59.6 |
| 20.7 | Polyethylene Oxide NF (MW 10,000) | 60.8 |
| 12.4 | Polyethylene Glycol 8000 NF | 36.5 |
| 12.4 | Sucrose NF | 36.6 |
| 2.6 | Silicon Dioxide NF | 7.5 |
| 805** | Methanol NF | 2370 |
| 288** | Acetone NF | 849 |
| 262** | Purified Water USP | 771 |

*Based on theoretical activity of 92%. The actual weight of erythromycin dihydrate used is calculated on a lot to lot basis according to the following formula:
Actual amount of erythromycin dihydrate to charge =

$$\frac{\text{Theoretical Amount to Charge* (92\%)}}{\text{Measured Activity (\%)}}$$

**Removed during processing

EXAMPLE 2

Reproducibility Study

Using the process described in Example 1, above, three batches of final product were manufactured. A 24-fold buildup of the starting seeds was used to produce the final product for each batch.

The final theoretical potency for each batch was approximately 730 mg/g. The final product of each batch was tested for potency and bulk density, and the results are set forth below in Table 2.

TABLE 2

| Batch | Bulk Density (G/ML) | Theoretical Potency (G/G) | Actual Potency (G/G) | Theoretical Activity Density (G/ML) | Actual Activity Density (G/ML) |
| --- | --- | --- | --- | --- | --- |
| 871103C | .638 | .728 | .737 | .464 | .470 |
| 871116A | .625 | .730 | .738 | .456 | .461 |
| 871117B | .640 | .732 | .726 | .468 | .468 |

The bulk densities, actual potencies and actual activity densities show a consistently reproducible final product. The average actual activity density for the three batches was 0.465 g/ml which was acceptable. This average value represents the average bulk density of the three batches multiplied by the average actual potency of the three batches.

EXAMPLE 3

Effect of Acetone/Methanol Ratio in the Enteric Coating Composition on the Dissolution Profile and Taste Mask Characteristics of the Final Product Three batches of erythromycin microencapsulated granules were manufactured following the procedure set forth in Example 1 above. However, the enteric coating composition of each batch was varied by the amount of acetone present in the solvent. Batch 871105A had an enteric coating composition solvent of 100% by weight acetone, Batch 871103C had an enteric coating composition solvent mixture of 75% by weight acetone and 25% by weight methanol, and Batch 871109A had an enteric coating composition solvent of 50% by weight acetone and 50% by weight methanol.

The dissolution of the final product of each batch was tested as well as the taste. The results of the test are set forth below in Table 3.

TABLE 3

| Batch | % Ct. Wt. | Time (min) | % Dissolved | Comments |
| --- | --- | --- | --- | --- |
| 871105A | 6 | 90 | *70.7 | Bitter taste |
| | | 120 | *85.5 | Acetone (100%) |
| 871103C | 6 | 90 | 79.3 | No taste |
| | | 120 | 95.6 | Ace/Meth (75/25) |
| 871109A | 6 | 90 | *76.3 | Slightly bitter |
| | | 120 | *87.8 | Ace/Meth (50/50) |

Dissolution testing for enteric coated pellets was performed as follows:
90 minutes = 60 minutes in simulated gastric fluid ("SGF") and 30 minutes in simulated intestinal fluid ("SIF").
120 minutes = 60 minutes in SGF and 60 minutes in SIF.
*Dissolution data based on theoretical potency. All other results based on measured potency.

The erythromycin microencapsulated granules with an enteric coating composition solvent comprising a mixture of 75% by weight acetone and 25% by weight methanol (Batch 871103C) not only had the best dissolution characteristics, but also had the best taste mask characteristics.

EXAMPLE 4

Stability of Erythromycin Microencapsulated Granules

Three batches of erythromycin microencapsulated granules were prepared in accordance with Example 1 (Batches 871103C-1, 871116A-1 and 871109A-1). Batches 871103C-1 and 871116A-1 were prepared with an enteric coating composition solvent comprising 75% by weight acetone and 25% by weight methyl alcohol.

However, Batch 871109A-1 was prepared with a mixture comprising 50% by weight acetone and 50% by weight methyl alcohol as the enteric coating composition solvent.

After manufacture, finished microgranules of each batch were sealed in prototype hiMedics, Inc.'s Flowable Material Dispensers (U.S. Pat. No. 4,579,256). Stability data was determined following storage at room temperature and at elevated temperature and humidity. The stability data for each batch (871103C-1, 871116A-1 and 871109A-1) is presented below in Tables 4A, 4B and 4C, respectively.

TABLE 4A

| Batch: #871103C-1 | | Batch Size (KG): 1.3 | | Theoretical Potency (mg/g): 723.0 |
|---|---|---|---|---|
| Parameter | Initial | 3 M RT | 6 M RT | Specifications |
| Potency (mg/g) | 726.0 | 823.0 | 769.0 | 658.0–840.0 act/gr |
| Potency (% Theory) | 99.7 | 113.0 | 105.6 | |
| Potency (% of Initial) | 100.0 | 113.4 | 105.9 | 90.0–115.0% LC |
| Loss of Dryness (% loss) | 0.35 | 0.64 | 0.93 | Report Value |
| Water (%) | 3.52 | 2.10 | 2.96 | Report Value |
| Appearance | Pass | Pass | Pass | Free Flowing White to Off-white Uniform Spheres |
| Odor | None | None | None | Report Odor |
| Taste | Pass | Pass | Pass | None to Slight Bitter |
| Bulk Density (g/ml) | 0.638 | 0.645 | 0.615 | Report Value |
| Dissolution Fluid: Acid & SIF @ 50 rpm Interval 120 mins (% Release) | 92.1 | 92.8 | 92.6 | NLT 80% @ 120 min |

| Parameter | Initial | 1 M 37/75 | 2 M 37/75 | 3 M 37/75 | 6 M 37/75 | Specifications |
|---|---|---|---|---|---|---|
| Potency (mg/g) | 726.0 | 739.0 | 784.0 | 796.0 | 759.0 | 658.0–840.0 act/gr |
| Potency (% Theory) | 99.7 | 105.5 | 107.7 | 109.3 | 104.3 | |
| Potency (% of Initial) | 100.0 | 101.8 | 108.0 | 109.6 | 104.5 | 90.0–115.0% LC |
| Loss of Dryness (% loss) | 0.35 | 1.96 | 2.24 | 1.80 | 2.73 | Report Value |
| Water (%) | 3.52 | 3.87 | 6.14 | 3.75 | 4.52 | Report Value |
| Appearance | Pass | Pass | Pass | Pass | Pass | Free Flowing White to Off-white Uniform Spheres |
| Odor | None | None | None | None | None | Report Odor |
| Taste | Pass | Pass | Pass | Pass | Pass | None to Slight Bitter |
| Bulk Density (g/ml) | 0.638 | 0.641 | 0.661 | 0.653 | 0.627 | Report Value |
| Dissolution Fluid: Acid & SIF @ 50 rpm Interval 120 mins (% Release) | 92.1 | 91.1 | 95.7 | 86.2 | 77.6 | NLT 80% @ 120 min |

Storage Conditions:
RT = Room Temperature 15–30° C.
37/75 = 35–40° C. with 70–80% Relative Humidity
M = Month

TABLE 4B

| Batch: #871116A-1 | | Batch Size (KG): 1.0 | | Theoretical Potency (mg/g): 730.00 |
|---|---|---|---|---|
| Parameter | Initial | 3 M RT | 6 M RT | Specifications |
| Potency (mg/g) | 761.0 | 733.0 | 752.0 | 658.0–840.0 act/gr |
| Potency (% Theory) | 104.2 | 105.8 | 103.0 | |
| Potency (% of Initial) | 100.0 | 105.4 | 98.8 | 90.0–115.0% LC |
| Loss of Dryness (% loss) | 0.05 | 0.35 | 0.50 | Report Value |
| Water (%) | 2.91 | 2.62 | 3.36 | Report Value |
| Appearance | Pass | Pass | Pass | Free Flowing White to Off-white Uniform Spheres |
| Odor | None | None | None | Report Odor |
| Taste | Pass | Pass | Pass | None to Slight Bitter |
| Bulk Density (g/ml) | 0.625 | 0.632 | 0.601 | Report Value |
| Dissolution Fluid: Acid & SIF @ 50 rpm Interval 120 mins (% Release) | 93.0 | 83.8 | 92.5 | NLT 80% @ 120 min |

| Parameter | Initial | 1 M 37.75 | 2 M 37.75 | 3 M 37/75 | 6 M 37/75 | Specifications |
|---|---|---|---|---|---|---|
| Potency (mg/g) | 761.0 | 734.0 | 766.0 | 798.0 | 764.0 | 658.0–840.0 act/gr |
| Potency (% Theory) | 104.2 | 105.5 | 104.9 | 109.3 | 104.7 | |
| Potency (% of Initial) | 100.0 | 96.5 | 100.7 | 104.6 | 100.4 | 90.0–115.0% LC |
| Loss of Dryness (% loss) | 0.05 | 2.17 | 1.89 | 1.55 | 2.47 | Report Value |
| Water (%) | 2.91 | 4.40 | 5.55 | 4.21 | 4.75 | Report Value |
| Appearance | Pass | Pass | Pass | Pass | Pass | Free Flowing White to Off-white Uniform Spheres |
| Odor | None | None | None | None | None | Report Odor |
| Taste | Pass | Pass | Pass | Pass | Pass | None to Slight Bitter |
| Bulk Density (g/ml) | 0.625 | 0.625 | 0.655 | 0.631 | 0.606 | Report Value |
| Dissolution Fluid: Acid & SIF @ 50 rpm Interval 120 mins | 93.0 | 90.2 | 93.5 | 88.4 | 74.8 | NLT 80% @ 120 min |

TABLE 4B-continued

Batch: #871116A-1  Batch Size (KG): 1.0  Theoretical Potency (mg/g): 730.00

(% Release)

Storage Conditions:
RT = Room Temperature 15-30° C.
37/75 = 35-40° C. with 70-80% Relative Humidity
M = Month

TABLE 4C

Batch: #871109A-1  Batch Size (KG): 1.2  Theoretical Potency (mg/g): 731.00

| Parameter | Initial | 3 M RT | 6 M RT | Specifications |
|---|---|---|---|---|
| Potency (mg/g) | 735.0 | 786.0 | 772.0 | 658.0-840.0 act/gr |
| Potency (% Theory) | 100.5 | 107.5 | 105.6 | |
| Potency (% of Initial) | 100.0 | 106.9 | 105.0 | 90.0-115.0% LC |
| Loss of Dryness (% loss) | 0.37 | 0.64 | 0.73 | Report Value |
| Water (%) | 2.98 | 3.02 | 3.56 | Report Value |
| Appearance | Pass | Pass | Pass | Free Flowing White to Off-white Uniform Spheres |
| Odor | None | None | None | Report Odor |
| Taste | Pass | Pass | Pass | None to Slight Bitter |
| Bulk Density (g/ml) | 0.651 | 0.621 | 0.590 | Report Value |
| Dissolution Fluid: Acid & SIF @ 50 rpm Interval 120 mins (% Release) | 90.4 | 83.6 | 83.7 | NLT 80% @ 120 min |

| Parameter | Initial | 1 M 37/75 | 2 M 37/75 | 3 M 37/75 | 6 M 37/75 | Specifications |
|---|---|---|---|---|---|---|
| Potency (mg/g) | 735.0 | 735.0 | 754.0 | 780.0 | 804.0 | 658.0-840.0 act/gr |
| Potency (% Theory) | 100.5 | 100.5 | 103.9 | 106.7 | 110.0 | |
| Potency (% of Initial) | 100.0 | 100.0 | 102.6 | 106.1 | 109.4 | 90.0-115.0% LC |
| Loss of Dryness (% loss) | 0.37 | 1.55 | 2.05 | 2.16 | 2.61 | Report Value |
| Water (%) | 2.98 | 3.97 | 4.77 | 4.46 | 3.84 | Report Value |
| Appearance | Pass | Pass | Pass | Pass | Pass | Free Flowing White to Off-white Uniform Spheres |
| Odor | None | None | None | None | None | Report Odor |
| Taste | Pass | Pass | Pass | Pass | Pass | None to Slight Bitter |
| Bulk Density (g/ml) | 0.651 | 0.644 | 0.670 | 0.636 | 0.617 | Report Value |
| Dissolution Fluid: Acid & SIF @ 50 rpm Interval 120 mins (% Release) | 90.4 | 81.3 | 82.5 | 82.2 | 76.2 | NLT 80% @ 120 min |

Storage Conditions:
RT = Room Temperature 15-30° C.
37/75 = 35-40° C. with 70-80% Relative Humidity
M = Month The stability data for all three batches was satisfactory, although it is clearly shown that the microgranules manufactured with a 75/25 weight % mixture of acetone and methyl alcohol as the solvent for the enteric coating composition (Batches 871103C-1 and 871116A-1) had better dissolution characteristics than the same microgranules manufactured with a 50/50 weight % mixture of acetone and methyl alcohol as the enteric coating composition solvent (Batch 871109A-1).

EXAMPLE 5

Effect of Percent Enteric Coat Weight on Dissolution and Taste Mask

Four batches of erythromycin microencapsulated granules were manufactured in accordance with the procedure set forth in Example 1 above. However, two batches (Batch 871112A and Batch 871113A) received a 4% by weight enteric coating and the other two batches (Batch 871116A and Batch 871117B) received a 6% by weight enteric coating. The differences in dissolution and taste mask were compared between the erythromycin granules with a 4% by weight enteric coating (Batches 871112A and 871113A) and the erythromycin granules with a 6% by weight enteric coating (Batches 871116A and 871117B). The results of the comparison are set forth in Table 5 below.

TABLE 5

| Batch | % Ct. Wt. | Time (min) | % Dissolved | Comments |
|---|---|---|---|---|
| 871112A | 4 | 90 | 75.8 | Bitter to slight Bitter taste |
| | | 120 | 89.9 | |
| 871113A | 4 | 90 | 78.7 | Very slight bitter taste |
| | | 120 | 93.0 | |
| 871116A | 6 | 90 | 90 | No taste |
| | | 120 | 95.0 | |
| 871117B | 6 | 90 | 79.0 | No taste |
| | | 120 | 94.0 | |

Dissolution analysis for enteric coated pellets was performed as follows:
90 minutes = 60 minutes in SGF and 30 minutes in SIF.
120 minutes = 60 minutes in SGF and 60 minutes in SIF.
*Dissolution analysis based on measured potency.

The 6% by weight enteric coated erythromycin (Batches 871116A and 871117B) displayed better dissolution characteristics and better taste mask characteristics than the erythromycin granules with a 4% by weight enteric coating (Batches 871112A and 871113A).

EXAMPLE 6

Granule Dissolution and Taste Mask Properties with Three Protective Coats and Methylene Chloride Enteric Coating Formulation Microencapsulated granules were prepared in accordance with Example 1 above. However, the enteric coating composition used to coat the seeds comprised 5% by weight hydroxypropyl methylcellulose phthalate in a solvent mixture of 75% by weight methylene chloride and 25% by weight methanol.

Dissolution and taste mask were tested for these granules in the same manner as in Example 5. The results of these tests are set forth below in Table 6.

TABLE 6

| Batch | % Ct./Wt. | Time (min.) | % Dissolved | Comment |
|---|---|---|---|---|
| 871030C | 6 | 90 | 85.7* | Slight bitter |
|  |  | 120 | 100.3* | to no taste |

*Dissolution data based on theoretical potency.

The dissolution characteristics and taste mask characteristics exhibited by the granules of this example were comparable to those exhibited by the granules of Example 5 (enteric coating composition with an acetone based solvent).

EXAMPLE 7

Pharmacokinetic Comparison of Erythromycin Dihydrate Microencapsulated Granules and a Conventional Erythromycin Product A twelve-hour bioavailability study was performed comparing erythromycin microencapsulated granules prepared in accordance with Example 1 above to an equivalent dose of a conventional erythromycin formulation, ERYC ® (registered trademark of Parke-Davis, Division of Warner-Lambert Company). The study was performed in the following manner.

Twenty-eight subjects were administered a single dose (250 mg) of each formulation (erythromycin microencapsulated granules and ERYC ®) in a randomized, cross-over food-fasted format with each dose separated by a 7-day washout period.

The subjects were healthy male and female volunteers, 21 to 39 years of age, and weighed within 10% of ideal body weight. Subjects were determined healthy by normal vital organ functions as reflected by medical history, physical examination, and laboratory tests. Females had negative serum pregnancy tests and were either surgically sterilized or using a reliable method of contraception.

The subjects were administered the erythromycin formulation with one teaspoonful of applesauce and 180 ml of water. Subjects with the standardized breakfast were administered the erythromycin formulation after finishing one Egg McMuffin ® then followed by one hot apple pie and the rest of the beverages (orange juice and coffee).

Five (5) ml of blood were collected prior to erythromycin administration, and then at 0.5, 1.0, 1.5, 2, 3, 4, 5, 6, 8, 10, 12 hours after administration. The blood was allowed to clot. Serum was separated by centrifugation within 60 minutes after collection. A seraclear filter was used to clarify the serum. Serum was placed in labelled polypropylene tubes and stored frozen at $-20°$ C.

Erythromycin concentrations were determined by microbiologic assay using *Micrococcus lutea*. An agar well procedure was performed in 10 mm sterile plastic petri plates containing Antibiotic Media #1 (Difco ®), adjusted to pH 8.5 before sterilization.

Mean pharmacokinetic parameters were determined from the samples of the subjects and are reported below in Table 7A.

A repeated measures analysis of variance was used to compare the four treatment regimens. Tukey's method posthoc multiple comparisons was used to compare mean values between two treatment regimens. P values are reported below in Table 7B (NS=Not Significant, $p > 0.05$).

TABLE 7A

| | Mean Pharmacokinetic Parameters | | | |
|---|---|---|---|---|
| | Regimen A | Regimen B | Regimen C | Regimen D |
| $C_{max}$ | 1.23 ± 0.58 | 1.16 ± 0.70 | 0.73 ± 0.55 | 0.50 ± 0.24 |
| $T_{max}$ | 3.06 ± 1.04 | 3.18 ± 0.89 | 5.82 ± 1.16 | 5.29 ± 1.00 |
| $T_{lag}$ | 2.02 ± 1.20 | 2.27 ± 0.80 | 4.32 ± 1.94 | 4.33 ± 1.17 |
| Ke | 0.424 ± 0.098 | 0.464 ± 0.168 | 0.45 ± 0.207 | 0.446 ± 0.129 |
| Half-Life | 1.72 ± 0.40 | 1.69 ± 0.61 | 1.64 ± 0.61 | 1.73 ± 0.66 |
| $AUC_{0-12}$ | 3.56 ± 1.92 | 3.01 ± 1.95 | 1.77 ± 1.40 | 1.46 ± 1.40 |
| $AUC_{0-\infty}$ | 4.16 ± 1.98 | 3.69 ± 1.95 | 2.55 ± 1.24 | 1.56 ± 0.76 |

Note:
Regimen A = granules without breakfast
Regimen B = ERYC ® without breakfast
Regimen C = granules with breakfast
Regimen D = ERYC ® with breakfast

TABLE 7B

| | $C_{max}$ | $T_{max}$ | $T_{lag}$ | $AUC_{0-12}$ |
|---|---|---|---|---|
| A to B | NS | NS | NS | NS |
| A to C | <0.05 | <0.05 | <0.05 | <0.05 |
| B to D | <0.05 | <0.05 | <0.05 | <0.05 |
| C to D | NS | NS | NS | NS |

Of the twenty-eight subjects enrolled, 26 completed the required four treatment regimens. Statistical significance was defined as a p value of 0.05. Statistical analysis of $AUC_{0-12}$, $C_{max}$, $T_{max}$, and $T_{lag}$ demonstrated no differences in relative oral bioavailability between the microencapsulated granule formulation of the present invention and ERYC ® capsule under either fasting or nonfasting conditions. The mean $AUC_{0-12}$ of Regimen A was 3.56 mghr/L compared to 3.01 mghr/L for Regimen B. The mean $C_{max}$, $T_{max}$, and $T_{lag}$ of Regimen A were similar to Regimen B. The mean $AUC_{0-12}$ of Regimen C was 1.77 mghr/L compared to 1.46 mghr/L for Regimen D. The mean $C_{max}$, $T_{max}$, and $T_{lag}$ were also similar. Administration of the microencapsulated granule formulation of the present invention or ERYC ® capsule with breakfast had a significant effect on relative oral bioavailability of both products. A decrease in $AUC_{0-12}$ of approximately 50% was seen with the granule formulation and ERYC ® capsule A statistically significant decrease in $C_{max}$ was also observed. The time to onset of absorption ($T_{lag}$) and peak concentration ($T_{max}$) were significantly prolonged with food.

Visual inspection of the serum erythromycin concentration v time curves demonstrated similar variability in the absorption of both products. In 36 of 104 concentration vs. time profiles, elimination rate constants could not be calculated, as there were inadequate data points clearly in the elimination phase. For this reason, statistical analysis of Ke, half-life, and $AUC_{0-12}$ was not performed. Food also significantly decreased $C_{max}$ and prolonged $T_{lag}$ and $T_{max}$ for both products.

EXAMPLE 8

Preparation of Microencapsulated Erythromycin Granules with Hydroxypropyl Methylcellulose E-5 as a Binder Microencapsulated granules were prepared (870102A) in accordance with Example 1 above. However, the active coating composition was composed of 4.5% (w/w) HPMC E-5 30.5% (w/w) Erythromycin and 65% (w/w) Methyl Alcohol. The starting seeds used were 40/60 mesh non-pareils. An 8-fold buildup of the starting seeds was used to produce the final product. The final theoretical potency was about 700 µg/mg (70%).

Although no attempt was made to use smaller starting seeds (60/80) or to perform a 24-fold buildup, this example indicates that HPMC E-5 is almost as good a binder as the polyethylene oxide/polyethylene glycol mixture. The results of these experiments are shown in Table 8. This binder produced yields of better than 90% in the desired size range at each of the processing steps (Active I, Active II and Active III).

EXAMPLE 9

Preparation of Microgranules of Erythromycin with Hydroxypropyl Methylcellulose E-15 as a Binder Microencapsulated granules were prepared (870120B) in accordance with Example 1 above. However, the active coating composition was composed of 2.1% (w/w) HPMC E-15, 32.7% (w/w) Erythromycin, 0.42% (w/w) PEG 400 and 64.8% (w/w) Methyl Alcohol. The starting seeds were 40/60 mesh non-pareils. An 8-fold buildup of the starting seeds was intended to produce the final product. The results of these experiments are shown in Table 8. This binder system did not produce active seeds resilient enough to withstand the extended processing time associated with the required high potency level. It is possible that alteration of processing conditions or the solvent system could improve the results so that a product of this nature might be deemed acceptable.

EXAMPLE 10

Preparation of Microgranules of Erythromycin with Hydroxypropyl Methylcellulose Phthalate HP 55S as a Binder Microencapsulated granules were prepared (870305B & 870312B) in accordance with Example 1 above. However, the active coating composition was composed of 2.8% (w/w) HPMCP HP 55S, 32.3% (w/w) Erythromycin, 52.3% (w/w) Methyl Alcohol, and 11.7% w/w Ethyl Acetate. The starting seeds used were 40/60 mesh non-pareils. An 8-fold buildup of the starting seeds was intended to produce the final product. The final theoretical potency was 699 µg/mg. The results of these experiments are shown in Table 8.

This binder produced yields of better than 90% in the desired size range at each of the processing steps. However, a high level of residual Ethyl Acetate was found (3.4% w/w). Although no attempt was made to use smaller starting seeds (60/80) or to perform a 24-fold buildup, this example indicates that HPMCP HP 55S is almost as good a binder as the polyethylene oxide/polyethylene glycol mixture. When Ethyl Acetate was removed from the solvent system, the binder did not produce active seeds resilient enough to withstand the extended processing times necessary for the high potency level. It is possible that further alteration of processing conditions or the solvent system could improve the results so that a product of this nature might be deemed acceptable.

EXAMPLE 11

Preparation of Microgranule of Erythromycin with Hydroxypropyl Cellulose as a Binder Microencapsulated granules were prepared (870116C) in accordance with Example 1 above. However, the active coating composition was composed of 2.5% (w/w) HPC, 32.5% (w/w) Erythromycin, and 65% (w/w) Methyl Alcohol. The starting seeds used were 40/60 mesh non-pareils. An 8-fold buildup of the starting seeds was intended to produce the final product. The results of these experiments are shown in Table 8. This binder did not produce active seeds resilient enough to withstand the extended processing time associated with the required high potency level. It is possible that alteration of processing conditions or the solvent system could improve the results so that a product of this nature might be deemed acceptable.

EXAMPLE 12

Preparation of Microgranules of Erythromycin with a 50/50 Mixture of HPMC E-15 and HPC Microencapsulated granules (870124B) were prepared in accordance with Example 1 above. However, the active coating composition was composed of 0.95% (w/w) HPMC E-15, 0.95% (w/w) HPC, 39.5% (w/w) Erythromycin, and 58.6% (w/w) Methyl Alcohol. The starting seeds used were 40/60 mesh non-pareils. An 8-fold buildup of the starting seeds was intended to produce the final product. The results of these experiments are shown in Table 8. This binder system did not produce active seeds resilient enough to withstand the extended processing time associated with the required high potency level. It is possible that further alteration of processing conditions or the solvent system could improve the results so that a product of this nature might be deemed acceptable

EXAMPLE 13

Preparation of Microgranules of Erythromycin with Polyvinyl-pyrrolidone as a Binder Microencapsulated granules were prepared (861226B) in accordance with Example 1 above. However, the active coating composition was composed of 4.55% (w/w) PVP K-30, 30.4% (w/w) erythromycin, and 65.0% (w/w) water. The starting seeds used were 40/60 mesh non-pareils. An 8-fold buildup of the starting seeds was intended to produce the final product. The results of this experiment are shown in Table 8.

This binder did not produce active seeds resilient enough to withstand the extended processing time associated with the required high potency level. It is possible that alteration of processing conditions or the solvent system could improve the results so that a product of this nature might be deemed acceptable.

of the batches, polyethylene oxide alone was used as the binder instead of the polyethylene oxide/polyethylene glycol mixture. Additionally, the processing of the microgranules was stopped at different stages and the granules were tested to determine their dissolution characteristics in simulated gastric fluid (SGF) and/or simulated intestinal fluid (SIF). Table 9, below shows the results of these tests.

TABLE 8

| Example | Binder | Lot No. | % Usable (within desired range) | % Recovered (amt. of material discharged) | Solvent System | (Stage of Active) | Comments |
|---|---|---|---|---|---|---|---|
| | | | ACTIVE I | | | | |
| 8 | HPMC E-5 | 861229A | 93.8 | 93.9 | Methanol | 1 of 3 | |
| 9 | HPMC E-15 | 870115A | 91.5 | 92.0 | Methanol | 1 of 3 | |
| 10 | HPMCP HP 55S | 870305B | 93.6 | 95.3 | Methanol/Ethyl Acetate (82%/18%) | 1 of 2 | |
| 11 | HPC | 870116C | 89.4 | 89.6 | Methanol | 1 of 3 | Did poorly in comparison to the other binders tested |
| 12 | HMPC E-15/HPC (50/50) | 870124B | 92.5 | 93.4 | Methanol | 1 of 3 | |
| 13 | PVP 29/32 | 861226B | 79.5 | 81.1 | Methanol | 1 of 3 | |
| 8 | HPMC E-5 | 861231A | 94.6 | 94.6 | Methanol | 2 of 3 | |
| 9 | HPMC E-15 | 870120B | 83.1 | 96.4 | Methanol | 2 of 3 | |
| 10 | HPMCP HP 55S | 870312B | 94.9 | 97.1 | Methanol/Ethyl Acetate (82%/18%) | 2 of 2 | |
| 11 | HPC | — | — | — | — | | This binder system showed inability to withstand further processing |
| 12 | HMPC E-15/HPC (50/50) | — | — | — | — | | This binder system showed inability to withstand further processing |
| 8 | HPMC E-5 | 870102A | 91.8 | 96.0 | Methanol | 3 of 3 | |
| 9 | HPMC E-15 | — | — | — | — | | This binder system showed inability to withstand further processing |
| 10 | HPMCP HP 55S | — | — | — | — | | This binder was used in an active process that required only two sets |
| 11 | HPC | — | — | — | — | | This binder system showed inability to withstand further processing |
| 12 | HMPC E-15 HPC (50/50) | — | — | — | — | | This binder system showed inability to withstand further processing |

NOTE:
The objective of a finished active product is an 8 to 1 weight gain. This was accomplished in a three step process with the exception of (HPMC-P H 55S) which required only two steps. Therefor, Active II (HPMC-P HP 55S) is equivalent to (HPMC E-5) Active III.

EXAMPLE 14

Effect of Polyethylene Oxide Binder Level in the Absence of Protective Coating Layers Erythromycin microencapsulated granules were prepared in accordance with Example 1. However, in some

TABLE 9

| Batch | Stage | Time | % Dissolution | % Ct Wt | Yield (%) | Comments |
|---|---|---|---|---|---|---|
| 871005C | Enteric | 90 min. | 34.7 | 8 | 69 | Act.: 8% binder (Polyox) |
| 871007A | Enteric | 90 min. | 34.5 | 15 | 97 | Act.: 8% binder (Polyox) |
| 871005A | Active | 30 min. | 69.4* | N/A | 96 | 8% binder (Polyox) |
| 871008D | Active | 30 min. | 106.6 | N/A | 69 | 5% binder (Polyox) |
| 871013B | Active | 30 min. | 94.0 | N/A | 92 | 8% binder (Polyox/PEG) |

TABLE 9-continued

| Batch | Stage | Time | % Dissolution | % Ct Wt | Yield (%) | Comments |
|---|---|---|---|---|---|---|
| 871017A | Acitve | 30 min. | 86.6* | N/A | 95 | 8% (Polyox/PEG),1 pr. ct |

Dissolution analysis for the active pellets was performed in SIF only.
Dissolution analysis for enteric coated pellets was performed as follows:
90 minutes = 60 minutes in SGF and 30 minutes in SIF
*Dissolution data based on theoretical potency. All other results based on measured potency.

The results shown above in Table 9 suggest a reaction between polyethylene oxide and erythromycin. The percentage of dissolution was unacceptably low in all the batches in which an 8% by weight polyethylene oxide binder was used (Batches 871005C, 871007A, 871005A). However, the lowering of the polyethylene oxide binder to 5% by weight resulted in a dissolution improvement, but the seeds were not resilient enough to withstand the extended processing time associated with the required high potency level as indicated by low values for yield (Batch 871008D).

Additionally, the mixture of polyethylene oxide and polyethylene glycol as a binder at 8% by weight resulted in microgranules with acceptable dissolution characteristics (Batch 871013A) but slightly reduced yield. The use of a polyethylene oxide/polyethylene glycol protective coating did slow the dissolution somewhat (see Batch 871017A) but raised yield slightly.

EXAMPLE 15

Comparison of Inventive Microgranules to ERYC® Granules

Table 10, below, compares the present inventive erythromycin microgranules to ERYC® erythromycin granules. The critical characteristics compared are size, potency, sphericity, bulk density and activity density.

TABLE 10

Inventive Microgranules to ERYC ® Granules

| | Screen Analysis Weight Percent Larger Than Stated Size | | | | | |
|---|---|---|---|---|---|---|
| | Mesh Size 14 | | | | | |
| | 16 | 18 | 20 | 25 | 30 | 35 |
| | | | Microns 1410 | | | |
| Product Name | 1190 | 1000 | 240 | 710 | 590 | 500 |
| ERYC ® (Erythromycin) | 66.5 | 29.2 | 3.1 | 0.5 | 0.2 | 0.1 |
| Present Invention (Erythromycin) (Batch 870309A) | | 5.0 | 49.0 | 36.0 | 8.0 | 2.0 |

| Product Name | Potency Weight % | Sphericity* Percent | Bulk Density | Activity Density |
|---|---|---|---|---|
| ERYC ® (Erythromycin) | 57.3 | 81.7 | 0.741 | 0.425 |
| Present Invention (Erythromycin) (Batch 870309A) | 67.4 | 90.5 | 0.668 | 0.450 |

*Sphericity was determined by a "cut and weigh" method. Photomicrographs were taken of individual particles. A template was then used to draw a circle circumscribing each particle. These circles were then cut out and weighed. Subsequently, the outline of the particle itself was cut out of the original circle and the remainder weighed. The weight of the remainder divided by the weight of the original circle and multiplied by 100 gave Sphericity Percent.

Table 10 indicates that presently available erythromycin granules do not meet all the required specifications of the present invention.

While the invention has been disclosed by reference to the details of various embodiments of the invention, it is understood that this disclosure is intended in an illustrative rather than in a limiting sense, as it is contemplated that modifications will occur to those skilled in the art, within the spirit of the invention and the scope of the appended claims.

What is claimed is:

1. A microencapsulated granule comprising a mixture of erythromycin and a binder as an active coating in a ratio of about 5:1 to about 15:1 on a seed, said granule having an activity density greater than about 0.300 g/ml and a diameter less than about 1000 microns, and said binder selected from the group consisting of hydroxypropyl methylcellulose phthalate, hydroxypropyl methylcellulose, polyvinyl pyrrolidone, polyethylene glycol, polyethylene oxide, hydroxypropyl cellulose, cellulose acetate phthalate, polyvinyl acetate phthalate and combinations thereof.

2. A dosage delivery system comprising a plurality of erythromycin microencapsulated granules as described in claim 1, contained in a unit dose delivery system.

3. The microencapsulated granule of claim 1 wherein the mixture is applied to the seed as an active coating composition comprising about 15% by weight to about 40% by weight erythromycin, about 1% by weight to about 4% by weight binder and a solvent.

4. The microencapsulated granule of claim 3 wherein the solvent may be selected from the group consisting of water, ethanol, methanol, isopropanol, acetone, methylene chloride, chloroform, ethyl acetate, carbon tetrachloride, benzene, methyl ethyl ketone and combinations thereof.

5. The microencapsulated granule of claim 1 further comprising a mixture of about 52% by weight to about 72% by weight polyethylene oxide and about 28% by weight to about 48% by weight polyethylene glycol applied as a protective coating over the active coating.

6. The microencapsulated granule of claim 5 wherein the protective coating is applied as a protective coating composition comprising about 10% by weight of the mixture of polyethylene oxide and polyethylene glycol and a solvent.

7. The microencapsulated granule of claim 6 wherein the solvent is water.

8. The microencapsulated granule of claim 5 further comprising an enteric coating over the protective coating, said enteric coating selected from the group consisting of cellulose acetate phthalate, polyvinyl acetate phthalate, acrylic resins, shellac, cellulose acetate butyrate, hydroxypropyl methylcellulose phthalate and combinations thereof.

9. The microencapsulated granule of claim 8 wherein the enteric coating comprises about 3% by weight to about 10% by weight hydroxypropyl methylcellulose phthalate.

10. The microencapsulated granule of claim 9 wherein the enteric coating is applied as an enteric coating composition comprising about 5% by weight to about 10% by weight hydroxypropyl methylcellulose phthalate and a solvent.

11. The microencapsulated granule of claim 10 wherein the solvent may be selected from the group consisting of acetone, a mixture of acetone and methanol and a mixture of methylene chloride and methanol.

12. The microencapsulated granule of claim 9 further comprising more than one active coating and more than one protective coating.

13. The microencapsulated granule of claim 12 wherein the active coatings and protective coatings are applied alternatively and in equal numbers.

14. The microencapsulated granule of claim 13 wherein three active coatings are applied and three protective coatings are applied.

15. The microencapsulated granule of claim 12 further comprising a sufficient amount of antistatic agent to coat the granule, said antistatic agent selected from the group consisting of silicon dioxide, talc, magnesium stearate, calcium stearate, polacrilin, stearic acid or combinations thereof.

16. The microencapsulated granule of claim 15 wherein the antistatic agent comprises about 0.75% by weight silicon dioxide.

17. A process for manufacturing an erythromycin microencapsulated granule having a ratio of erythromycin to a binder of about 5:1 to about 15:1, an activity density greater than about 0.300 g/ml and a diameter less than about 1000 microns, comprising:
 (a) applying an active coating composition to an inert seed to form an active seed; and
 (b) applying a protective coating composition to the active seed;
  said active coating composition comprising about 15% by weight to about 40% by weight erythromycin, about 1% by weight to about 4% by weight binder and a solvent; and
  said protective coating composition comprising about 10% by weight of a mixture of polyethylene oxide and polyethylene glycol and a solvent.

18. A process for manufacturing erythromycin microencapsulated granules comprising:
 (a) applying an active coating composition to an active drug crystal to form an active seed; and
 (b) applying a protective coating composition to the active seed;
  said active coating composition comprising about 5% by weight to about 40% by weight erythromycin, about 1% by weight to about 4% by weight binder and a solvent; and
  said protective coating composition comprising about 10% by weight of a mixture of polyethylene oxide and polyethylene glycol and a solvent.

19. The process of claim 17 wherein:
 the binder may be selected from the group consisting of hydroxypropyl methylcellulose phthalate, hydroxypropyl methylcellulose, polyvinylpyrrolidone, polyethylene glycol, polyethylene oxide, hydroxypropyl cellulose, cellulose acetate phthalate, polyvinyl acetate phthalate and combinations thereof;
 the solvent for the active coating composition and may be selected from the group consisting of water, ethanol, methanol, isopropanol, acetone, methylene chloride, chloroform, ethyl acetate, carbon tetrachloride, benzene, methyl ethyl ketone and combinations thereof;
 the solvent for the protective coating composition is water; and
 the protective coating composition mixture of polyethylene oxide and polyethylene glycol comprises about 52% by weight to about 72% by weight polyethylene oxide and about 28% by weight to about 48% by weight polyethylene glycol.

20. The process of claim 19 further comprising more than one active coating composition application and more than one protective coating composition application.

21. The process of claim 20 wherein the active coating composition and protective coating composition are applied alternatively and in equal numbers.

22. The process of claim 21 wherein the active coating composition and the protective coating composition are each applied three times.

23. The process of claim 22 further comprising applying an enteric coating composition after the last application of protective coating composition.

24. The process of claim 23 wherein the enteric coating composition comprises about 5% by weight to about 10% by weight hydroxypropyl methylcellulose phthalate and a solvent.

25. The process of claim 24 wherein the solvent may be selected from the group consisting of acetone, a mixture of acetone and methanol and a mixture of methylene chloride and methanol.

26. The process of claim 23 further comprising applying a sufficient amount of an antistatic agent to coat the microgranules.

27. The process of claim 26 wherein the antistatic agent may be selected from the group consisting of silicon dioxide, talc, magnesium stearate, calcium stearate, polacrilin, stearic acid and combinations thereof.

28. The process of claim 26 wherein the active coating composition, the protective coating composition, the enteric coating composition and the antistatic agent are applied by use of a fluidized bed technique.

29. A dosage delivery system comprising a plurality of erythromycin microencapsulated granules as described in claim 1, in a tablet form.

30. A dosage delivery system comprising a plurality of erythromycin microencapsulated granules as described in claim 1 contained in a water soluble capsule.

31. A dosage delivery system comprising a plurality of erythromycin microencapsulated granules as described in claim 1 contained in a flowable material dispenser.

* * * * *